US008821424B2

(12) United States Patent
Alleyne

(10) Patent No.: US 8,821,424 B2
(45) Date of Patent: *Sep. 2, 2014

(54) SPINAL ORTHOSIS TO INHIBIT KYPHOSIS AND TO MINIMIZE DISK DISEASE

(76) Inventor: Neville Alleyne, La Jolla, CA (US)

(*) Notice: Subject to any disclaimer, the term of this patent is extended or adjusted under 35 U.S.C. 154(b) by 74 days.

This patent is subject to a terminal disclaimer.

(21) Appl. No.: 13/432,335

(22) Filed: Mar. 28, 2012

(65) Prior Publication Data

US 2012/0184888 A1 Jul. 19, 2012

Related U.S. Application Data

(63) Continuation of application No. 12/652,630, filed on Jan. 5, 2010, now Pat. No. 8,147,437, which is a continuation of application No. 11/271,490, filed on Nov. 10, 2005, now Pat. No. 7,654,972.

(60) Provisional application No. 60/627,389, filed on Nov. 12, 2004.

(51) Int. Cl.
*A61F 5/00* (2006.01)

(52) U.S. Cl.
USPC .................. 602/19; 602/4; 602/5; 602/20

(58) Field of Classification Search
USPC ............. 602/5, 19, 4, 20; 128/845, 846, 869, 128/874; 482/122, 124
See application file for complete search history.

(56) References Cited

U.S. PATENT DOCUMENTS

| 369,803 A | 9/1887 | McComber |
|---|---|---|
| 3,029,810 A | 4/1962 | Martin |
| 3,548,817 A | 12/1970 | Mittasch |
| 4,570,619 A | 2/1986 | Gamm |
| 5,135,470 A | 8/1992 | Reeves |
| 5,319,806 A | 6/1994 | Hermann et al. |
| 5,462,518 A | 10/1995 | Hatley et al. |
| 5,651,764 A | 7/1997 | Chiu |
| 5,685,831 A | 11/1997 | Floyd |
| 5,816,251 A | 10/1998 | Glisan |
| 5,855,561 A | 1/1999 | Glidden |
| 5,876,361 A | 3/1999 | Harris |
| 5,950,628 A | 9/1999 | Dunfee |
| 6,190,342 B1 | 2/2001 | Taylor |
| 6,213,922 B1 | 4/2001 | Afanasenko et al. |
| 7,445,608 B2 | 11/2008 | Dunfee et al. |
| 7,654,972 B2 * | 2/2010 | Alleyne ..................... 602/19 |
| 2009/0030359 A1 | 1/2009 | Wikenheiser et al. |
| 2009/0036888 A1 | 2/2009 | Dunfee et al. |

* cited by examiner

*Primary Examiner* — Kim M Lewis
(74) *Attorney, Agent, or Firm* — Knobbe Martens Olson & Bear LLP

(57) ABSTRACT

In one embodiment, a spinal orthosis includes a left shoulder portion and a right shoulder portion connected to a retracting device through a retractable connector. The retractable connector is connected, at a first end, to the left shoulder portion and the right shoulder portion and is connected at a second end to the retracting device. The retractable connector is configured to pull the left shoulder portion and the right shoulder portion so as to move the shoulders of a patient in a rearward direction. The retractable connector is further configured to release the left shoulder portion and the right shoulder portion, thereby allowing the shoulders of the patient to return to a relaxed position.

15 Claims, 2 Drawing Sheets

SPINAL ORTHOSIS TO INHIBIT KYPHOSIS AND TO MINIMIZE DISK DISEASE

CROSS-REFERENCE TO RELATED APPLICATIONS

This application is a continuation of U.S. patent application Ser. No. 12/652,630, filed Jan. 5, 2010, which is a continuation of U.S. patent application Ser. No. 11/271,490, filed Nov. 10, 2005, issued as U.S. Pat. No. 7,654,972 on Feb. 2, 2010, which claims priority under 35 U.S.C. §119(e) of U.S. Provisional Application No. 60/627,389, filed Nov. 12, 2004 for "SPINAL BRACE TO INHIBIT KYPHOSIS AND TO MINIMIZE DISK DISEASE." The disclosures of the above-referenced prior applications, publications, and patents are considered part of the disclosure of this application, and are incorporated by reference herein.

BACKGROUND OF THE INVENTION

1. Field of the Invention

The present invention relates to the field of orthotics. More specifically it relates to an orthosis applied to the spine to help prevent progressive kyphosis.

2. Description of the Related Art

As one of skill in the art of orthopedic spine surgery, or orthopedics, will recognize, patients, especially older patients in their late 60s, 70s, 80s and older, may have developed painful progressive kyphosis, and have become dependent on assistive devices for ambulation such as, for example, a cane, Canadian crutches, a walker or a wheelchair. Many of these patients have developed this deformity from a myriad of different conditions, some of which are: poor posture, compression fractures secondary to osteoporosis or other metabolic bone diseases (e.g., osteomalacia, traumatic burst fractures or compression fractures), iatrogenic topping off phenomenon (in which adjacent cephalad segments to a fusion have developed, and collapsed into kyphosis), ligament injuries leading to instability and progressive kyphosis, and degenerative disk disease leading to thoracolumbar kyphoscoliosis and/or flat back syndrome, etc. It is the job of an orthopedic spine surgeon to become aware of this condition and try to intervene. Such methods of intervention have included: a reminder by the spouse or friend to improve posture, intervention with physical therapy for postural strengthening exercises, intermittent brace immobilization, (e.g., a Jewett orthosis, a TLSO (thoracolumbar spinal orthosis), a Cash orthosis, or lumbosacral corsets, etc), involvement in work out classes (e.g., weight lifting, yoga, Pilates, tae chi, marshal arts, etc.), but all of these act only as temporary measures. The kyphosis usually continues to occur leading to increased deformity, difficulty ambulating and the need many times for an assistive device and use of medications and/or surgery to correct the deformity.

Braces that have been used in the thoracolumbar sacral region tend to be cumbersome and may not be worn for long periods of time because of poor patient compliance and failure of the brace to maintain or prevent the progression of the kyphotic deformity. If the braces are worn 24 hours a day, seven days a week, this would lead to an inevitable atrophy of the paraspinous musculature, and increase susceptibility to fracture due to the loss in nutrition to the spine and vertebral column because of the degree of immobilization. Rigid braces, such as the TLSO, could lead to atrophy also of the thoracic cavity which could result in diminished respiratory tidal volume, as well as decrease tone of the abdominal musculature and thoracolumbar musculature, as well as decreasing the thoracic and lumbar bone density which could lead to compression fractures, which could lead to back pain and/or instability.

As well as being used for treating the elderly, braces may also be used to accommodate young populations that may be at risk. Young people may be at risk due to, e.g., carrying heavy books to school, as well as for rapidly developing young women who have developed a postural kyphosis to minimize their enlargement of their breasts, or in the male population in which the thin or esthetic young male who is not physically developed and has poor posture, can use this orthosis to improve their sagittal spinal contour.

It is estimated by some that 80% of the about 285 million people in the United States may injure their backs at some point in time necessitating them seeing a physician. It is the premise of some medical professionals that most disk disease and back pain may occur at a very early age from poor end plate nutrition to the disk, as well as from weakened paraspinous musculature and/or poor posture from and early age, e.g, from preteen all the way up to an adult. After 40, especially in the female population, the incidence of osteoporosis starts to become a significant factor, and this continues all the way up into the elderly. This is manifested also with a failure in the later population for exercising and performing good paraspinous muscle strengthening and the natural degenerative process of aging of the disks which leads to loss in disk height, decrease in disk hydration and increase in annular tears, as well as protrusions from the nucleus pulposus, as well as ligament instability leading to anterior listhesis, retrolisthesis, lateral listhesis or rotatory deformity.

As the population grows older, there is a loss in the disk space height over several levels which may lead to several inches lost in height. Therefore, a person who is six feet tall at age twenty, by the time they are eighty, could end up being five feet ten inches tall. The loss in height of the lumbar spine and thoracic vertebrae may result in a structural change.

As obesity has approached an epidemic proportion in the United States, some statistics show about two-thirds of all Americans are officially overweight, and among those that are overweight, about 50% are obese, and close to about 5% are morbidly obese. With the number of children becoming more and more inactive due to, e.g., TV, computer and video games and their access to junk food, this trend may continue to increase with secondary medical conditions, such as hypertension, diabetes, heart disease, which may continue to escalate costs for medical care. It is estimated at this point in time that approximately 117 billion dollars a year is spent on obesity-linked illnesses.

As a person becomes older it is typically more difficult for them to engage in cardiovascular exercise and exercise for the spine if this is something that the person has not started at an earlier age. Some patients, especially the elderly, may find it difficult to do much more than just walk. In some cases, the addition of one or two exercises in conjunction with the walking is not kept up after the patient has completed physical therapy.

Due to these trends, there is a need for an orthosis that may passively allow the spine and paraspinous muscles to work with little effort, thereby encouraging a patient to wear the orthosis so as to prevent poor posture, to prevent progressive kyphosis, to prevent juvenile round back syndrome, to decrease back pain and to assure appropriate spinal integrity as the patient ages.

SUMMARY OF THE INVENTION

A spinal orthosis used to prevent progressive thoracic kyphosis, prevent vertebral compression fractures, decrease disk degeneration, increase end plate blood flow, increase paraspinous muscle blood flow, and increase paraspinous muscle and ligament strength. The device is worn with pads anterior to the shoulder which are light weight, with a strap that extends onto a lumbar or sacral belt which is capable of shortening and lengthening to stimulate mild hyperextension of the thoracolumbar spine.

DETAILED DESCRIPTION OF CERTAIN EMBODIMENTS

Figure 1:
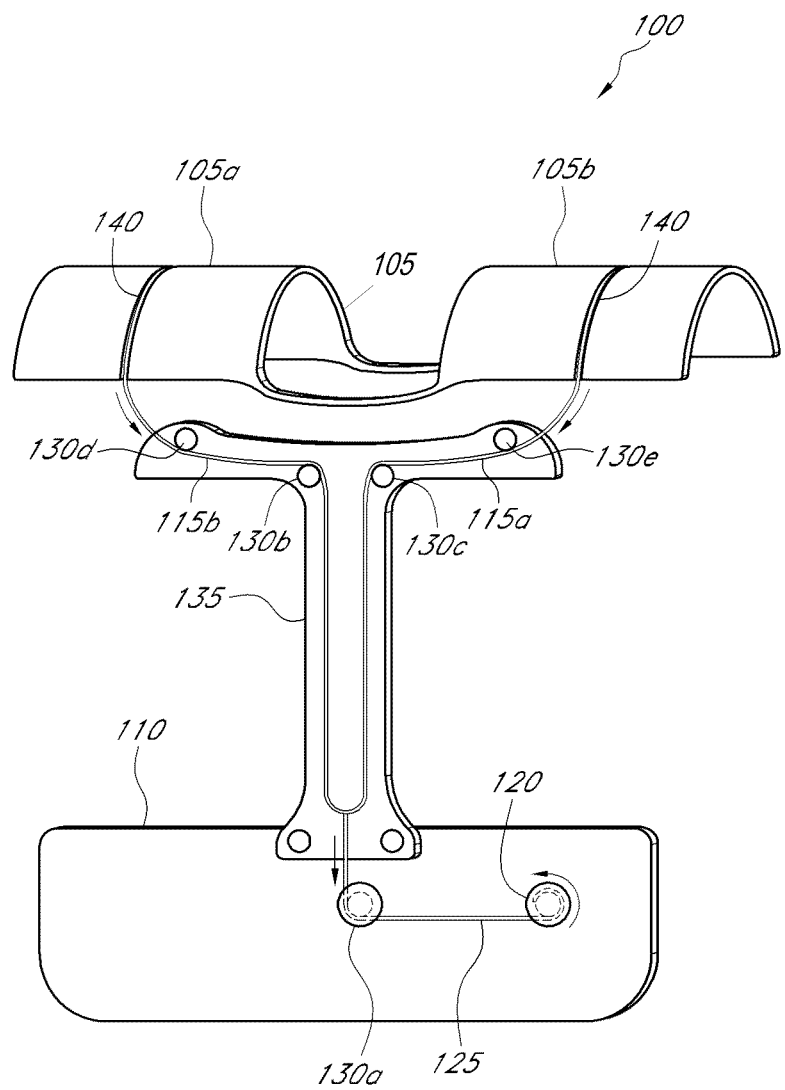
FIG. 1 is a view of one embodiment of a spinal orthosis.

Aspects of the present invention will be described with respect to particular embodiments and with reference to certain drawings but the invention is not limited thereto but only by the claims. The drawings described are only illustrative and are non-limiting. In the drawings, the size of some of the elements may be exaggerated and not drawn on scale for illustrative purposes.

Furthermore, the terms first, second, third, and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under, and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

An embodiment of the invention relates to an orthotic device, or orthosis, applied to a patients spine to help prevent progressive kyphosis. An orthosis may be considered to be any external orthopedic device that prevents or assists the movement of the spine and/or limbs. The orthosis is designed to allow for a rearward extension of the shoulders by contracting or retracting a connecting means which extends from a shoulder portion to a lumbosacral belt. The retracting can occur within the belt by tightening the connecting means that connects the shoulder pad portion to the lumbosacral belt. In one embodiment, the retracting takes place at variable intervals, e.g., about ten repetitions per hour, to stimulate the paraspinous musculature which may indirectly stimulate blood flow to the vertebral end plates and to the paraspinous musculature. By retracting a pre-set amount the brace may be capable of generating a force of mild extension of the shoulders which would translate into decreasing thoracic kyphosis and possibly increasing lumbar or lordosis and improving posture.

In one embodiment, the spinal orthosis mechanism for timing contractions comprises a timer with a retracting device that is built into the belt. The connecting cable attaches to the belt which then pulls the cable from both ends, right and left, which would uniformly contract and cause the shoulder to be pulled backwards, forcing the chest to come out, and decreasing the thoracic kyphosis. Since the lumbosacral unit is fixed along the pelvis, this would also slightly increase the lumbar lordosis.

In a preferred embodiment, the orthosis is worn temporarily thereby possibly enhancing spinal musculature, enhancing vertebral body density, improving thoracic kyphosis and lumbar lordosis and decreasing the progression of degenerative disk disease by increasing blood flow to the cartilaginous end plates which feed the disks by a process known as imbibition.

The orthosis may come in sizes for adults and be light weight with a belt that can be worn that is quite inconspicuous. The orthosis may also be worn by elderly population with osteoporosis or post op spinal fusion to prevent kyphotic deformity. Because the orthosis is light weight and easy to apply, and is inconspicuous with one's clothing, there will be little reason for noncompliance, as opposed to the more traditional heavy, cumbersome and conspicuous braces that are presently being utilized.

In elderly patients, the natural degenerative process of aging of the disks may lead to loss in disk height, decrease in disk hydration and increase in annular tears, as well as protrusions from the nucleus pulposus, as well as ligament instability leading to anterior listhesis, retrolisthesis, lateral listhesis or rotatory deformity. Use of the orthosis may prevent progressive deformity. It may also provide for paraspinous muscle strengthening. Use of the orthosis may also stimulate blood flow to the end plates, the primary nutrition for the disk would thereby increase, and this may decrease the rate of disk degeneration.

FIG. 1 is a view of one embodiment of a spinal orthosis. In this embodiment the spinal orthosis 100 includes a shoulder pad unit 105 comprising a left shoulder portion 105*a* and a right shoulder portion 105*b*, which may be applied over both shoulders of a patient. The anterior portion of the pads provide for a comfortable support in the deltopectoral region. A thin band 140 goes around the top of the clavicle and upper portion of the scapula, which is then linked in the back to connectors 115*a* and 115*b* that run along the spinous processes. The connectors 115*a* and 115*b* may be encased in a plastic tubing, referred to herein as a connector arm 135, that then gets attached to a lumbosacral unit 110 (a belt in this embodiment). A retractable connector 125 engages the connectors 115*a* and 115*b* in the spinal portion of the connector arm 135. The retractable connector 125 is then attached to a retracting device 120. The connectors 115*a* and 115*b*, and the retractable connector 125 may be guided through the connector arm 135 by various guiding means 130*a* through 130*e*. The guiding means may be pulleys, ratchets, or plastic or metal guides configured to allow the connectors 115*a* and 115*b* and the retractable connector 125 to translate around the corners in the connector arm channel and the lumbosacral unit 110.

The shoulder portions 105*a* and 105*b* may be secured to the patient's shoulders by straps or by a pressure fit, depending on the embodiment. In another embodiment the shoulder pad unit 105 may comprise two straps (one for each shoulder) that go around the shoulders and attach at both ends of the two straps to the connectors 115*a* and 115*b*. In another embodiment, the shoulder portions 105*a* and 105*b* may be separate units (not joined across the neck area as in the embodiment shown in FIG. 1) that are held onto the shoulders by securing means such as, for example, straps that pass under the shoulders, e.g., at the armpits.

The shoulder portions 105*a* and 105*b* may come in multiple sizes such as, e.g., small, medium and large, for individuals with different size and shape. In one embodiment, the anterior deltopectoral region of the shoulder will be the area that is used for pulling the shoulders back. The device may be predominantly kept off of the bony structures, such as the clavicle, acromion or greater tuberosity of the humerus. By pulling on the more muscular fat pad of the deltopectoral region, the gentle retraction of the connectors 115a and 115b may not apply a painful force to those aforementioned regions.

In one embodiment, the connector arm 135 is a thin, flat belt or tube that has two cables or wires running in it that gets attached to the lumbosacral unit 110. The retracting device 120 may then pull on the connectors 115a and 115b through a series of guides (e.g., pulleys, guide posts or ratchets, as discussed above).

The embodiment shown in FIG. 1 includes a T-shaped connector arm 135. In another embodiment, the T-shaped connector arm may be replaced by a single connector arm channel that simply parallels the spine and where the connectors 115a and 115b enter at the top of the channel (near where the guides 130b and 130c are positioned in FIG. 1).

The connectors 115a and 115b may be any of several forms including straps, cables, wires, flexible tubing, wires, and others. The material of the connectors 115a and 115b may be any material that is strong enough to withstand the tensile force of pulling back on the shoulders, such as plastic, cloth, metal, nylon and others. The thin band 140 may comprise the same, similar or different materials and forms as the connectors 115a and 115b. The retractable connector 125 may also comprise the same, similar or different materials and forms as the connectors 115a and 115b.

The lumbosacral unit 110 may comprise a belt made of a light weight plastic, polyethylene, polypropylene, neoprene, metal, such as stainless steel, titanium, aluminum, or nylon as well as others that are known to those of skill in the art. The belt serves as an anchoring point of attachment for the retractable connector 125 and/or the connectors 115a and 115b that run down the back and connect to the lumbosacral unit 110 to provide a fixed point that does not move substantially and is connected in such a way that, preferably, the only part that is pulling is the retraction of the connectors 115a and 115b from the shoulder portion to the lumbosacral region. With the belt in place, very minimal vertical displacement may be seen, and during the times of retraction the belt may be kept secure. During the other times the belt may be slightly loosened. The connection for the belt can be a simple buckle, seat belt clasp, or spring-loaded clasp.

In another embodiment, the lumbosacral unit 110 takes the form of thigh cuffs instead of a belt The thigh cuffs may perform the same anchoring as the belt, but attached to the thighs. The retracting device 120 may be positioned on either or both thigh cuffs or positioned in the connector arm 135 structure.

In one embodiment, retracting device 120 comprises an electric motor (e.g., an electric motor powered by a battery pack) to provide retraction or shortening of the cable system (illustrated by the arrows along the connectors 115a, 115b and the retractable connector 125 in the embodiment shown in FIG. 1) which then gives rise to a force being applied to the anterior portion of the shoulders, which then pulls the shoulders back and creates a reduction in thoracic kyphosis and an increase in lumbar lordosis.

For every centimeter of shortening of the retractable connector 125, there is a correlated displacement of shoulder portions 105a and 105b. Increasing the amount of displacement will then increase the force across the anterior portion of the shoulder, which then pulls the shoulders back, decreasing the thoracic kyphosis and increasing lumber lordosis. This dynamic motion allows the spine to go through a work out without the individual having to initiate and perform the exercise himself. This indirect passive movement of the shoulders into extension is what will increase the paraspinous muscle strength, and the paraspinous blood flow, and thereby increase cartilaginous end plate nutrition.

In one embodiment, the retracting device 120 includes a wheel, located on either the right or left side of the belt, that is turned, thereby simultaneously shortening the connectors 115a and 115b. This wheel turning may engage the retractable connector 125 which will pull on the connectors 115a and 115b, or in another embodiment, the wheel may engage the connectors 115a and 115b directly, thereby applying a force to the anterior deltopectoral area to pull the shoulders backwards.

In one embodiment, the orthosis 100 includes a lumbar pad attached to it to increase the lumbar lordosis. In one embodiment, the lumbar pad is attached to the lumbosacral unit 110, or the connector arm 135. The pad may be attached with a hook and loop-type fastener, such as Velcro®, so that it may be temporarily attached and then removed.

Figure 2:
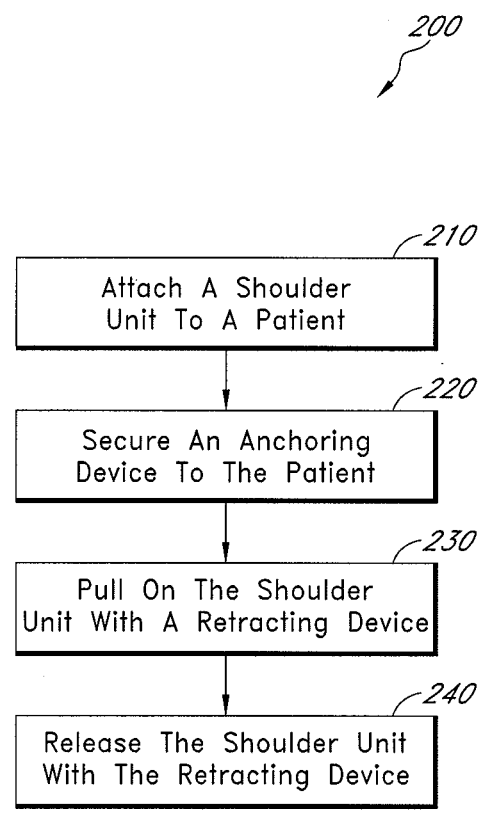
FIG. 2 is a flow diagram illustrating certain steps in an embodiment of a method for treating a patient.

FIG. 2 shows a flow diagram illustrating certain steps in an embodiment of a method for treating a patient with, e.g., an orthosis as described above. The method 200 may be performed by the patient theirself, by a trained therapist, by a medical doctor, or by a person trusted by the patient. The method 200 may be performed using an orthosis similar to the embodiment shown in FIG. 1 or by any of several other embodiments of orthosis that may perform similar actions, as would be known to one of skill in the art.

With reference to FIGS. 1 and 2, the method 200 starts by attaching a shoulder unit 105 to a patient's shoulders at step 210. The shoulder unit 105 comprises shoulder portions 105a and 105b that may be secured such that the shoulder portions 105a and 105b pull on the anterior portion of the patients shoulders without significant slippage. Attaching means such as straps or a pressure fit may be used to attach the shoulder portion 105a and 105b. Method 200 continues at step 220 where an anchoring device, such as the lumbosacral belt 110, is secured to a lower body region of the patient so as to prevent substantial vertical motion of the anchoring device when the shoulder units are pulled in step 230. In one embodiment, the anchoring device comprises thigh cuffs. The anchoring device contains a retracting device 120 such as an electric motor or a manual crank. When the retracting device 120 is actuated, the retracting device retracts connectors 115a and 115b which are attached to the left shoulder portion 105a and the right shoulder portion 105b, respectively, thereby pulling on the shoulder unit at step 230. The pulling results in the shoulders being extended rearward. After maintaining the shoulders in a retracted position, the retracting device 120 is released at step 240, thereby allowing the shoulders to return to their relaxed position (or a slightly retracted position). Steps 230 and 240 may be repeated a number of times to increase the paraspinous muscle strength, and the paraspinous blood flow, and thereby increase cartilaginous end plate nutrition In one embodiment the retraction step 230 and release step 240 may be timed such that, once the device is attached and secured, it contracts and releases for about 20 repetitions in one minute. This may repeated every hour, as long as the orthosis is connected. What this process does is to force the spine gently into extension and relaxation, and this movement is what stimulates the paraspinous muscles which thereby increases the blood flow to that region which then stimulates the blood flow to the cartilaginous end plates. The disk, as one of skill in the art is aware, is an avascular structure, which receives most of its nutrition from the cartilaginous end plates by the process known as imbibition. This diffusion of the nutrients to the disk space is supported by the nutritional integrity of that cartilaginous end plate. The early forms of degeneration, including loss in hydration, annular tears, loss in disk height and loss in elasticity, may be due, at least in part, to poor end plate blood flow and nutrition. It is therefore the purpose of this spinal orthosis to increase that blood flow, thereby increasing the nutrition to the disk, and as a result, decreasing the rate of disk degeneration. The contractions of 20 to 30 repetitions over a minute may be enough to stimulate the paraspinous musculature for increased blood flow. In one embodiment the retracting device 120 maintains the shoulders in a retracted position of improved posture when the repetition of steps 230 and 240 is completed. The retracted position being a position of decreased thoracic kyphosis and increased lumbar lordosis.

In one embodiment, method 200 may be controlled with an on/off switch. This on/off switch may have a built in potentiometer which will give out a reading of the amount of force being applied to the shoulders. An output display connected to the potentiometer may comprise three areas, a green area, a yellow area and a red area. A gentle retraction and a corresponding force may read in the green area, a more significant retraction and the corresponding force may read in the yellow area, and a severe retraction and the corresponding force may read in the red region. Again, these retractions may comprise about 20 to 30 repetitions over a period of a minute, giving rise to a maneuver which one could reproduce either standing or sitting, lying, pushing his chest forward and throwing his shoulders back repeatedly. This motion, if practiced routinely, by an individual, would increase blood flow to the paraspinous musculature. However, with the spinal orthosis of the invention, this particular maneuver is being done in a more passive way.

In one embodiment, after steps 230 and 240 have been completed about 20 to 30 times, there is a cut off switch in electrical communication with the retracting device 120 so as to deactivate the method 200. The reason for this is so as not to over work the musculature or strain the paraspinous muscles. It may be recommended that initially during a patient's first few weeks, the device should be kept at a very low setting and as the muscles become stronger, a higher setting can be utilized. In another embodiment, the retracting device on/off timing is configured to be monitored by a processor to identify how long each day the orthosis is being worn. The processor may store the timing information in a memory to be retrieved later.

In one embodiment, a spinal orthosis includes shoulder means for attaching to a right shoulder and a left shoulder of a body, first means for pulling back on the shoulder means when the first pulling means is retracted, the first pulling means being connected to the shoulder means attached to the left shoulder and second means for pulling back on the shoulder means when the second pulling means is retracted, the second pulling means being connected to the shoulder means attached to the right shoulder. The orthosis further includes means for retracting the first pulling means and the second pulling means, the retracting means attached to the first pulling means and the second pulling means, and means for securing the retracting means, the retracting means being attached to the securing means, the securing means being attached to the body below a lower back area. With reference to FIG. 1, aspects of this embodiment include where the shoulder means are shoulder pads such as the shoulder portions 105*a* and 105*b*, where the first and second pulling means are cables such as connectors 115*a* and 115*b*, where the retracting means is an electric motor such as retracting device 120, and where the securing means is a lumbrosacral belt such as lumbosacral unit 110.

While the above detailed description has shown, described, and pointed out novel features of the invention as applied to various embodiments, it will be understood that various omissions, substitutions, and changes in the form and details of the device or process illustrated may be made by those skilled in the art without departing from the spirit of the invention. As will be recognized, the present invention may be embodied within a form that does not provide all of the features and benefits set forth herein, as some features may be used or practiced separately from others.

What is claimed is:

1. A spinal orthosis comprising a left shoulder portion and a right shoulder portion connected to a retracting device through a retractable connector, the retractable connector being connected, at a first end, to the left shoulder portion and the right shoulder portion and being connected at a second end to the retracting device, the retractable connector configured to pull the left shoulder portion and the right shoulder portion so as to move the shoulders of a patient in a rearward direction, the retractable connector further configured to release the left shoulder portion and the right shoulder portion, thereby allowing the shoulders of the patient to return to a relaxed position.

2. The spinal orthosis of claim 1, wherein the retracting connector is configured to pull and release the left shoulder portion and the right shoulder portion repeatedly.

3. The spinal orthosis of claim 1, wherein the retracting device is configured to retract the retractable connector to pull the left shoulder portion and the right shoulder portion, and wherein the retracting device is further configured to release the retractable connector to release the left shoulder portion and the right shoulder portion.

4. The spinal orthosis of claim 3, wherein the retracting device is configured to retract and release the retractable connector about 20 to 30 times in one minute.

5. The spinal orthosis of claim 1, wherein the retracting device includes an electric motor.

6. The spinal orthosis of claim 5, further comprising a battery pack electrically connected to the electric motor.

7. The spinal orthosis of claim 5, further comprising:
a timer; and
a switch in electrical communication with the timer and the electric motor, the switch configured to enable the retracting device to retract and to release alternately after a first time period has elapsed.

8. The spinal orthosis of claim 7, wherein the switch is further configured to disable the retracting device after the retracting device has been enabled for a second time period.

9. The spinal orthosis of claim 8, further comprising:
a memory; and
a processor in electrical communication with the switch and the timer, the processor being configured to receive timing data from the timer indicating when the switch enabled and disabled the retracting device, and to store the timing data in the memory.

10. The spinal orthosis of claim 1, further comprising a lumbar pad positioned so as to increase lumbar lardosis.

11. The spinal orthosis of claim 1, further comprising:
a battery pack; and
a potentiometer in electrical connection with the battery pack, the potentiometer configured to output a voltage indicating a tensile force of the retractable connector.

12. The spinal orthosis of claim 1, further comprising an anchoring device connected to the left shoulder portion and the right shoulder portion through the retractable connector.

13. The spinal orthosis of claim 12, wherein the anchoring device comprises a belt adapted to be attached to the patient below a lower back area.

14. The spinal orthosis of claim 12, further comprising a connector arm attached to the anchoring device at a first end of the connector arm and providing a channel for the retractable connector.

15. The spinal orthosis of claim 12, further comprising a connector arm comprising a first arm portion with a proximal end of the first arm portion attached to the anchoring device, the connector arm further comprising a second arm portion attached to a distal end of the first arm portion and extending toward the left shoulder portion, and the connector arm further comprising a third arm portion attached to the distal end of the first arm portion and extending toward the right shoulder portion.

\* \* \* \* \*